United States Patent
Lai

(10) Patent No.: US 12,295,658 B2
(45) Date of Patent: May 13, 2025

(54) CONCISE REPRESENTATION FOR REVIEW OF A SUBJECTIVE REFRACTION TEST

(71) Applicant: Shui T Lai, Windermere, FL (US)

(72) Inventor: Shui T Lai, Windermere, FL (US)

(*) Notice: Subject to any disclaimer, the term of this patent is extended or adjusted under 35 U.S.C. 154(b) by 562 days.

(21) Appl. No.: 17/589,376

(22) Filed: Jan. 31, 2022

(65) Prior Publication Data

US 2022/0330811 A1    Oct. 20, 2022

Related U.S. Application Data

(63) Continuation of application No. 16/379,790, filed on Apr. 9, 2019, now Pat. No. 11,234,588.

(60) Provisional application No. 62/806,911, filed on Feb. 18, 2019, provisional application No. 62/793,366, filed on Jan. 16, 2019, provisional application No. 62/655,193, filed on Apr. 9, 2018.

(51) Int. Cl.
| | |
|---|---|
| *A61B 3/02* | (2006.01) |
| *A61B 3/00* | (2006.01) |
| *A61B 3/028* | (2006.01) |
| *A61B 3/032* | (2006.01) |
| *A61B 3/036* | (2006.01) |
| *G16H 10/60* | (2018.01) |

(52) U.S. Cl.
CPC .............. *A61B 3/02* (2013.01); *A61B 3/0075* (2013.01); *A61B 3/028* (2013.01); *A61B 3/032* (2013.01); *A61B 3/036* (2013.01); *G16H 10/60* (2018.01)

(58) Field of Classification Search
CPC ......... A61B 3/02; A61B 3/0075; A61B 3/028; A61B 3/032; A61B 3/036; G16H 10/60; G16H 10/20; G16H 40/63; G16H 50/20

USPC ......................................... 351/222, 227, 246
See application file for complete search history.

(56) References Cited

U.S. PATENT DOCUMENTS

| | | | | |
|---|---|---|---|---|
| 4,105,302 A | * | 8/1978 | Tate, Jr. ................ | A61B 3/028 351/210 |
| 5,280,491 A | | 1/1994 | Lai | |
| 5,549,632 A | | 8/1996 | Lai | |

(Continued)

FOREIGN PATENT DOCUMENTS

| | | |
|---|---|---|
| WO | 03/034909 A2 | 5/2003 |
| WO | 2014/083392 A1 | 6/2014 |

(Continued)

OTHER PUBLICATIONS

PCT Notification of transmittal of the international search report and the written opinion of the international searching authority, or the declaration, for PCT Application No. PCT/US2020/018712, filed Feb. 18, 2020.

(Continued)

*Primary Examiner* — William R Alexander
(74) *Attorney, Agent, or Firm* — SF Bay Area Patents, LLC; Andrew V. Smith

(57) ABSTRACT

A concise representation illustrating essential elements of a subjective refraction eye test that includes choices of optics offered to a test subject, responses by the test subject indicating respective choices among the optics, and time durations of, between, or both of and between, responses by the test subject indicating the respective choices of optics. The concise representation includes a presentation that illustrates the essential elements of the eye test.

26 Claims, 11 Drawing Sheets

(56) References Cited

U.S. PATENT DOCUMENTS

| | | |
|---|---|---|
| 5,914,772 A * | 6/1999 | Dyer ............... A61B 3/028 351/222 |
| 5,984,916 A | 11/1999 | Lai |
| 6,210,401 B1 | 4/2001 | Lai |
| 6,325,792 B1 | 12/2001 | Swinger et al. |
| 6,706,036 B2 | 3/2004 | Lai |
| 6,761,454 B2 | 7/2004 | Lai et al. |
| 7,114,415 B1 | 10/2006 | Chiang |
| 7,114,808 B2 | 10/2006 | Lai et al. |
| 7,220,255 B2 | 5/2007 | Lai |
| 7,234,810 B2 | 6/2007 | Warden et al. |
| 7,293,871 B2 | 11/2007 | Dreher et al. |
| 7,420,743 B2 | 9/2008 | Lai et al. |
| 7,425,067 B2 | 9/2008 | Warden et al. |
| 7,461,938 B2 | 12/2008 | Lai |
| 7,490,940 B2 | 2/2009 | Dreher et al. |
| 7,695,134 B2 | 4/2010 | Dreher et al. |
| 7,699,471 B2 | 4/2010 | Lai |
| 7,726,811 B2 | 6/2010 | Lai |
| 7,748,844 B2 | 7/2010 | Lai |
| 7,824,033 B2 | 11/2010 | Lai |
| 7,909,461 B2 | 3/2011 | Warden et al. |
| 7,954,950 B2 | 6/2011 | Dreher et al. |
| 7,959,284 B2 | 6/2011 | Lai |
| 8,033,664 B2 | 10/2011 | Lai |
| 8,066,359 B2 | 11/2011 | Silverbrook et al. |
| 8,113,658 B2 | 2/2012 | Warden et al. |
| 8,262,220 B2 | 9/2012 | Lai |
| 8,366,274 B2 | 2/2013 | Lai |
| 8,388,137 B2 | 3/2013 | Dreher et al. |
| 8,409,177 B1 | 4/2013 | Lai |
| 8,632,183 B2 | 1/2014 | Lai |
| 8,632,184 B2 | 1/2014 | Lai |
| 8,636,359 B2 | 1/2014 | Warden et al. |
| 8,684,527 B2 | 4/2014 | Warden et al. |
| 8,753,551 B2 | 6/2014 | Lai |
| 8,790,104 B2 | 7/2014 | Lai |
| 8,950,865 B2 | 2/2015 | Lai |
| 8,967,801 B2 | 3/2015 | Lai |
| 9,247,871 B2 | 2/2016 | Lai |
| 9,277,857 B1 | 3/2016 | Berme et al. |
| 9,320,426 B2 | 4/2016 | Lai |
| 9,408,533 B2 | 8/2016 | Lai |
| 9,730,578 B2 | 8/2017 | Lai |
| 9,743,829 B2 | 8/2017 | Lai |
| 10,194,794 B2 | 2/2019 | Lai |
| 10,194,796 B2 | 2/2019 | Lai |
| 10,383,512 B2 | 8/2019 | Lai |
| 11,234,588 B2 | 2/2022 | Lai |
| 11,464,406 B2 | 10/2022 | Lai |
| 2003/0117580 A1 | 6/2003 | Franz et al. |
| 2006/0023163 A1 | 2/2006 | Foster |
| 2006/0217688 A1 | 9/2006 | Lai |
| 2006/0290885 A1 | 12/2006 | Covannon et al. |
| 2008/0039825 A1 | 2/2008 | Lai |
| 2008/0208363 A1 | 8/2008 | Grgic et al. |
| 2008/0212024 A1 | 9/2008 | Lai |
| 2008/0246922 A1 | 10/2008 | Blum et al. |
| 2009/0310084 A1 | 12/2009 | Foster |
| 2012/0050685 A1 | 3/2012 | Bartlett et al. |
| 2012/0120369 A1 | 5/2012 | Lai |
| 2013/0339043 A1 | 12/2013 | Bakar et al. |
| 2014/0218692 A1 * | 8/2014 | Nordstrom ............ A61B 3/0041 351/242 |
| 2014/0285769 A1 * | 9/2014 | Palanker ................ G16H 40/67 351/246 |
| 2015/0022782 A1 | 1/2015 | Hofeldt |
| 2015/0216411 A1 * | 8/2015 | Gaton ..................... G02C 7/085 351/246 |
| 2016/0128893 A1 | 5/2016 | Ooi |
| 2016/0310001 A1 | 10/2016 | Lai |
| 2017/0188816 A1 | 7/2017 | Ono et al. |
| 2017/0228521 A1 | 8/2017 | Appakaya et al. |
| 2018/0070811 A1 | 3/2018 | Lai |
| 2018/0092525 A1 | 4/2018 | Lai |
| 2018/0136486 A1 | 5/2018 | Macnamara et al. |
| 2019/0183330 A1 | 6/2019 | Schiffman et al. |
| 2020/0397281 A1 | 12/2020 | Pundlik et al. |
| 2023/0218160 A1 | 7/2023 | Lai |

FOREIGN PATENT DOCUMENTS

| | | |
|---|---|---|
| WO | 2020/172203 A1 | 8/2020 |
| WO | 2021/167647 A1 | 8/2021 |

OTHER PUBLICATIONS

PCT Invitation to Pay Additional Fees, form ISA/206, dated Dec. 30, 2020, for PCT Application No. PCT/US2020/048304, filed Aug. 27, 2020, 3 pages.

PCT Notification of transmittal of the international search report and the written opinion of the international searching authority, or the declaration, dated Mar. 17, 2021, for PCT Application No. PCT/US2020/048304, filed Aug. 27, 2020, 36 pages.

* cited by examiner

| Test Part # | Part Seq. # | Time | Choice | Optic Power |
|---|---|---|---|---|
| 1 | 1 | 11 | 0 | -0.845 |
| 1 | 2 | 4 | 0 | -0.595 |
| 1 | 3 | 4 | 0 | -0.345 |
| 1 | 4 | 4 | 0 | -0.095 |
| 1 | 5 | 4 | 0 | 0.155 |
| 1 | 6 | 5 | -1 | 0.405 |
| 2 | 1 | 6 | 0 | 100 |
| 2 | 2 | 6 | 0 | 100 |
| 3 | 1 | 12 | 1 | 0.47 |
| 3 | 2 | 7 | 1 | 0.97 |
| 3 | 3 | 5 | -1 | 1.47 |
| 3 | 4 | 5 | -1 | 1.22 |
| 3 | 5 | 7 | 0 | 0.97 |
| 3 | 6 | 6 | 1 | -0.845 |
| 3 | 7 | 6 | 0 | -0.595 |
| 4 | 1 | 13 | 0 | -0.885 |
| 4 | 2 | 5 | 0 | -0.635 |
| 4 | 3 | 4 | 0 | -0.385 |
| 4 | 4 | 4 | 0 | -0.135 |
| 4 | 5 | 4 | 0 | 0.115 |
| 4 | 6 | 9 | -1 | 0.365 |
| 5 | 1 | 6 | 1 | 91 |
| 5 | 2 | 5 | 1 | 96 |
| 5 | 3 | 5 | 1 | 101 |
| 5 | 4 | 7 | 0 | 106 |
| 5 | 5 | 6 | 0 | 106 |
| 6 | 1 | 19 | -1 | -0.89 |
| 6 | 2 | 32 | 1 | -1.14 |
| 6 | 3 | 10 | 1 | -1.015 |
| 6 | 4 | 6 | -1 | -0.89 |
| 6 | 5 | 6 | 0 | -0.9525 |

Figure 3

| Test Part # | Part Seq. # | Time | Choice | Optical Power |
|---|---|---|---|---|
| 1 | 1 | 13 | 0 | -5.525 |
| 1 | 2 | 5 | 0 | -5.275 |
| 1 | 3 | 4 | 0 | -5.025 |
| 1 | 4 | 5 | 0 | -4.775 |
| 1 | 5 | 4 | -1 | -4.525 |
| 2 | 1 | 5 | 0 | 155 |
| 3 | 1 | 19 | -1 | 0.19 |
| 3 | 2 | 9 | 1 | -0.31 |
| 3 | 3 | 5 | 1 | -0.06 |
| 3 | 4 | 7 | 0 | 0.19 |
| 4 | 1 | 10 | 0 | -5.065 |
| 4 | 2 | 3 | 0 | -4.815 |
| 4 | 3 | 4 | -1 | -4.565 |
| 5 | 1 | 5 | 0 | 158 |
| 6 | 1 | 13 | 1 | -0.99 |
| 6 | 2 | 6 | 1 | -0.74 |
| 6 | 3 | 5 | 1 | -0.49 |
| 6 | 4 | 6 | 1 | -0.24 |
| 6 | 5 | 6 | 0 | 0.01 |

Figure 4

CONCISE REPRESENTATION FOR REVIEW OF A SUBJECTIVE REFRACTION TEST

PRIORITY AND RELATED APPLICATIONS

This application is a Continuation of U.S. patent application Ser. No. 16/379,790, filed Apr. 9, 2019, now U.S. Pat. No. 11,234,588; which claims the benefit of priority to U.S. provisional patent applications Nos. 62/655,193, filed Apr. 9, 2018; 62/793,366, filed Jan. 16, 2019; and 62/806,911, filed Feb. 18, 2019; each of which are hereby incorporated by reference.

The present application is related to U.S. Pat. Nos. 9,743,829, 9,730,578, 9,408,533, 9,320,426, 9,247,871, 8,967,801, 8,950,865, 8,684,527, 8,632,184, 8,632,183, 8,409,177, 8,388,137, 8,366,274, 8,262,220, 8,113,658, 8,033,664, 7,959,284, 7,954,950, 7,909,461, 7,824,033, 7,748,844, 7,726,811, 7,699,471, 7,695,134, 7,490,940, 7,461,938, 7,425,067, 7,293,871, 7,114,808, 6,706,036, 6,210,401, 5,280,491, 5,549,632, and 5,984,916, and to published United States patent applications nos.: 2018/0092525, 2018/0070811, 2008/0039825, 2008/0208363, 2008/0212024, 2016/0310001, 2006/0217688.

Each of the above patents and published patent applications is incorporated by reference.

BACKGROUND

Traditionally, an ophthalmologist, physician, or an optometrist, or a technician, sits with a patient during an eye exam for the entirety of the test. The time taken by the physician, optometrist or physician's assistant or other authorized trained person is the duration of the entire test. The physician, optometrist or trained technician is highly skilled and highly compensated. Their time is valuable and therefore, the testing time is very expensive. It is desired to reduce the amount of time spent by the physician, optometrist or technician and/or to eliminate, replace or substitute with less expensive personnel for at least some of the testing time would be beneficial.

One way to achieve this would be to record the whole process on an audio and/or video recording. However, recording takes the same amount of time. Moreover, whoever reviews the audio and/or video recording would take the same amount of time as sitting through the entire test. It is desired to have a way of presenting the essential elements of a test to a physician, optometrist and/or other skilled person or technician that takes significantly less time than a duration of a subjective refraction test.

BRIEF DESCRIPTION OF THE DRAWINGS

FIG. 3 includes an example of a table as stand-alone concise representation or as one component of a concise representation of a subjective refraction eye test indicating numerically essential elements of another example subjective refraction eye test for ascertaining sphere, cylinder and astigmatism or axis angle aberrations for right and left eyes of a test subject in accordance with certain embodiments.

FIG. 4 includes an example of a table as a stand-alone concise representation or as one component of a concise representation indicating numerically essential elements of another example subjective refraction test for a test subject's right and left eyes for ascertaining sphere, cylinder and astigmatism or axis angle aberrations in accordance with certain embodiments.

DETAILED DESCRIPTION OF THE EMBODIMENTS

Figure 1A:
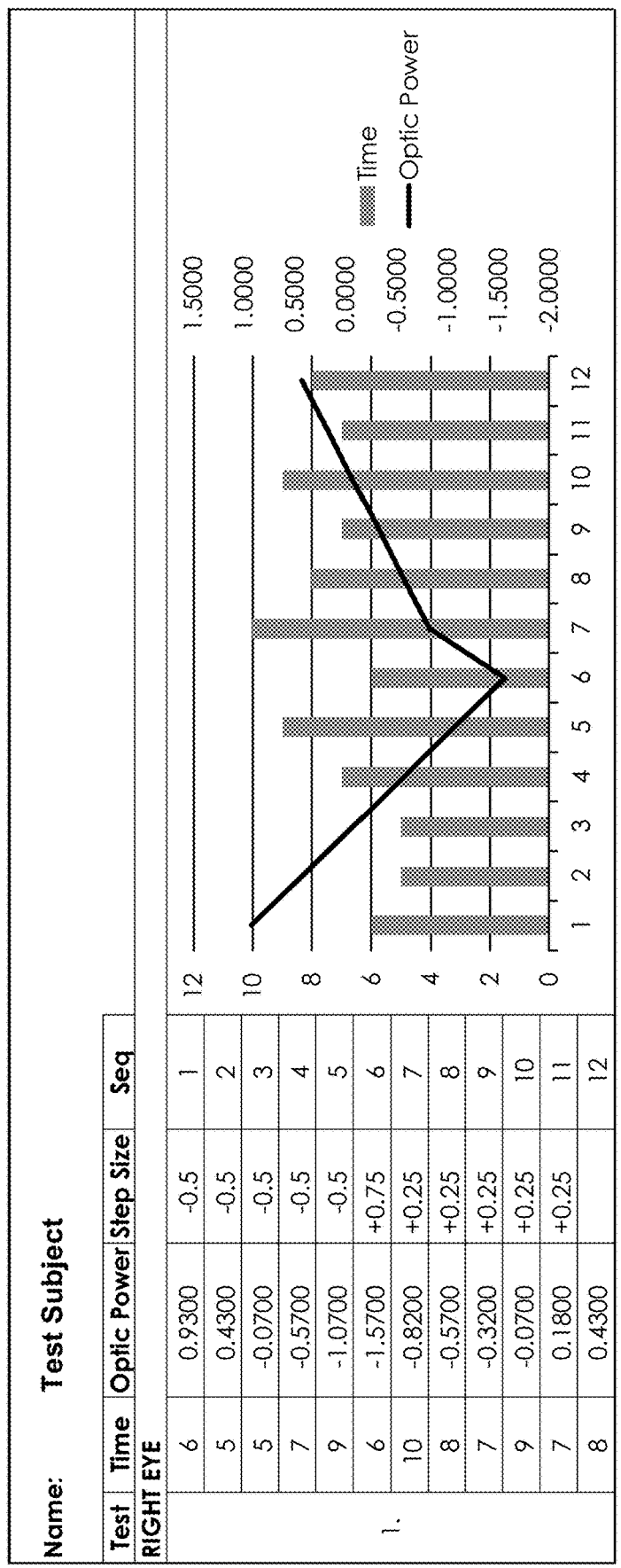
FIG. 1A includes an example of a table indicating numerically certain essential elements, including optical power and test subject response time and step size for an example subjective refraction eye test for ascertaining aberrations of sphere for a right eye of a test subject in accordance with certain embodiments.

Several embodiments including example methods of preparing a concise representation of a subjective refraction eye test for review by an optometrist or physician are provided. For the purpose of referring to the authorized refractionists, such as ophthalmologist, optometrist, physician's assistant, or other authorized refraction technicians, they may be referred to as refraction experts throughout the specification or in the claims. Essential elements of a subjective refraction eye test are captured. Essential elements include choices of optics offered to the patient, responses of the patient indicating a choice among said optics, and time durations taken by the patient for each response. A concise representation of the test is generated. The concise representation includes a presentation that illustrates the essential elements of the refraction test.

Some example embodiments are particularly suited to apply to telemedicine, where one highly trained; skilled physician may be at a remote location, and the physician may be overseeing multiple locations where patients are to be refracted or treated. The utility and efficiency of the physician is greatly enhanced. The costs to each test subject of having the benefit of a highly skilled, highly educated and highly compensated physician overseeing their subjective refraction eye test in real time can be significantly reduced when the physician contemporaneously oversees one or more additional eye tests occurring at spaced apart locations. Alternatively, the physician may attend only a subset of the entire test, e.g., at the end of the subjective refraction eye test, or after the test is finished, either right afterwards before the test subject leaves the testing area or significantly later at a scheduled conference call date and time, when in each case a concise representation of data gathered during the eye test is generated and provided to the physician who can digest the test results quicker when provided in an efficient illustrative format that highlights the essential elements and their impact on the test subject's quality of vision so that diagnostic or prognostic options may be gleaned in a fraction of the time it typically takes to run the entire eye test. Such concise representation is generated from the raw data gathered in the eye test and processed in accordance with scientifically proved formulas such that the concise representation is reliable as being based in science.

A concise representation may be configured in accordance with certain embodiments to provide a compact, e.g., a single 8.5×11 single or double-sided summary of the data gathered during the subjective refraction eye test, or perhaps two or three pages, including one to six graphs, plots, charts, or other presentations of comparative or standardized eye test data that allows a physician or optometrist or skilled eye care technician a condensed, brief and information report that includes all o the essential elements needed for the physician to opine as to treatments or other next steps. Since all essential elements of a test are presented in a concise representation to the physician, it provides the physician the benefits of experiencing what exactly happened, without being physically present at the location.

The presentation may include one or more charts, plots, and/or graphs that each illustrate one or more of the essential elements. The presentation may include one or more charts, plots and/or graphs for each of the left and right eyes of the patient. The presentation may include one or more charts, plots and/or graphs for compensating the refractive errors in the sphere, cylinder and axis for each of the left and right eyes of the patient.

The presentation may include one or more tables indicating numerically an optical power of each of the choices of optics offered to the patient, the patient's response indicating a choice among said optics, and the time durations of each response of the patient. The presentation may include one or more tables indicating numerically an optical power of each of the choices of optics offered to the patient and the time durations of each response of the patient for each of left and right eyes of the patient. The presentation may include one or more tables indicating numerically an optical power of each of the choices of optics offered to the patient and the time durations of each response of the patient for compensating the refractive errors in the sphere, cylinder, and axis for each of the left and right eyes of the patient.

The presentation may include a bar chart illustrating the time durations of each response by the patient. The presentation may also include a plot of optical powers of each of the choices of optics offered to the patient, and the patient's response indicating a choice among said optics. Slopes of the plot may illustrate step sizes of changes in optical power between successive choices of optics offered to the patient.

The presentation may include a bar chart illustrating the time durations of each response of the patient overlaying the plot of optical powers. The data points may be equally spaced along the x-axis, or alternatively, the data points may be spaced along the x-axis in accordance with the response times.

The essential elements may include step sizes of changes in optical power between successive choices of optics offered to the patient, and the patient's response indicating a choice among said optics.

The method may also include communicating the concise representation to an optometrist or physician, the refraction expert.

The method may also include performing a subjection refraction eye test.

The presentation may include a continuous audio recording or assembly of audio clips of patient responses to said choices of optics overlaying a graphical presentation illustrating said choices of optics or said patient response times or both.

The presentation may include a continuous video recording or assembly of video clips or a slide show of still images showing patient responses to the choices of optics.

The presentation may include a continuous video recording or assembly of video clips or a slide show of still images showing patient responses to the choices of optics overlaying a graphical presentation illustrating the choices of optics or the patient response times or both.

The method may also include compressing the presentation for remote storage, transmission to an optometrist or physician, display or editing or combinations thereof.

One or more non-transitory processor-readable digital storage devices are also provided in accordance with certain embodiments. The one or more devices have code embedded therein for programming a processor to perform a method of preparing a concise representation of a subjective refraction eye test for review by an optometrist or physician according to any of the example embodiments describe above or below herein.

A processor-based device is also provided herein that includes a processor, one or more non-transitory processor-readable digital storage devices having code embedded therein for programming said processor to perform a method of preparing a concise representation of a subjective refraction eye test for review by an optometrist or physician according to any of the example embodiments describe above or below herein, and electronics configured for one or more of transmitting, displaying, storing, translating or editing the concise representation of the subjective refraction eye test for review by the optometrist or physician.

The essential elements may include step sizes of changes in optical power between successive choices of optics offered to the patient. Reviewer may see a trend or a correlation of optics step size versus the duration in the response in the test, thereby building a better refraction test to the patient in general.

The concise digital representation may include a continuous audio recording or assembly of audio clips of patient responses to the choices of optics overlaying a graphical presentation illustrating the choices of optics or the patient response times or both. The concise digital representation may include a continuous video recording or assembly of video clips or a slide show of still images showing patient responses to the choices of optics.

The concise digital representation may include a continuous video recording or assembly of video clips or a slide show of still images showing patient responses to the choices of optics overlaying a graphical presentation illustrating the choices of optics or the patient response times or both.

Figure 1B:
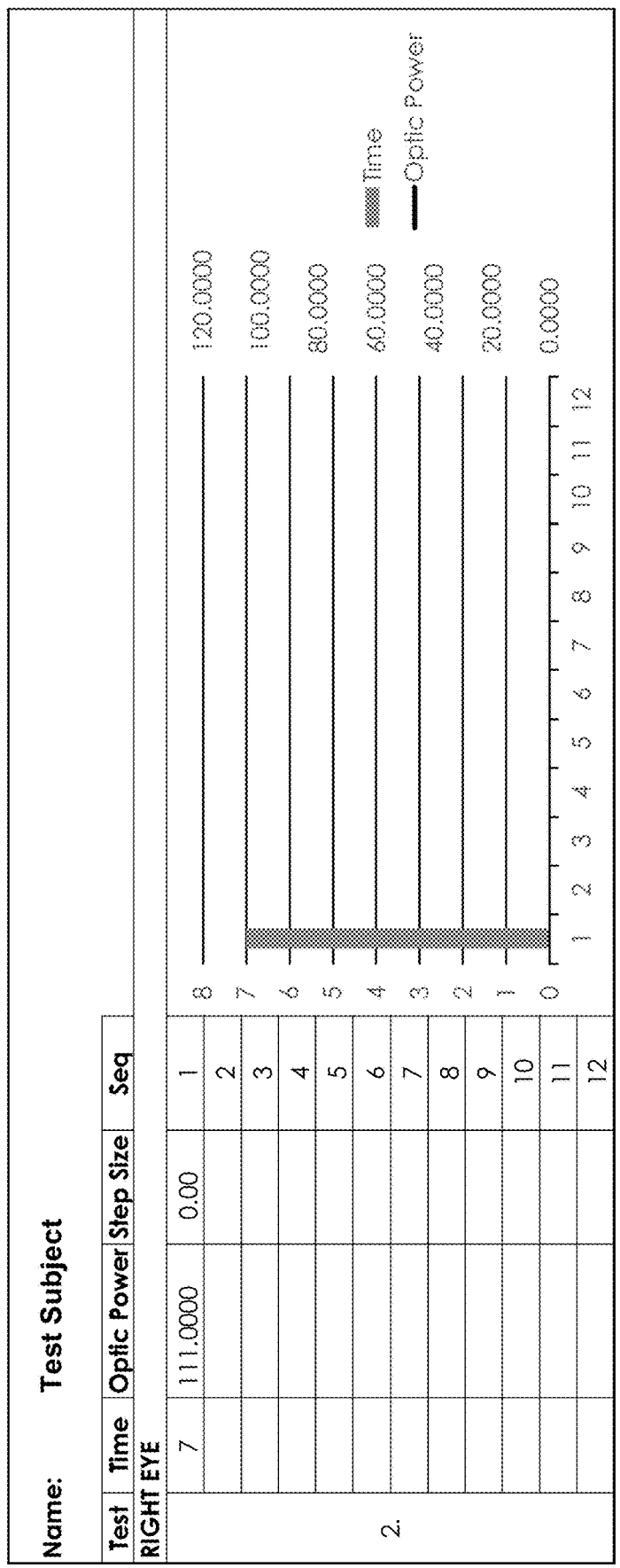
FIG. 1B includes an example of a table indicating certain numerically essential elements, including optical power and test subject response time and step size for an example subjective refraction test for ascertaining cylinder aberrations for a right eye of a test subject in accordance with certain embodiments
Figure 1C:
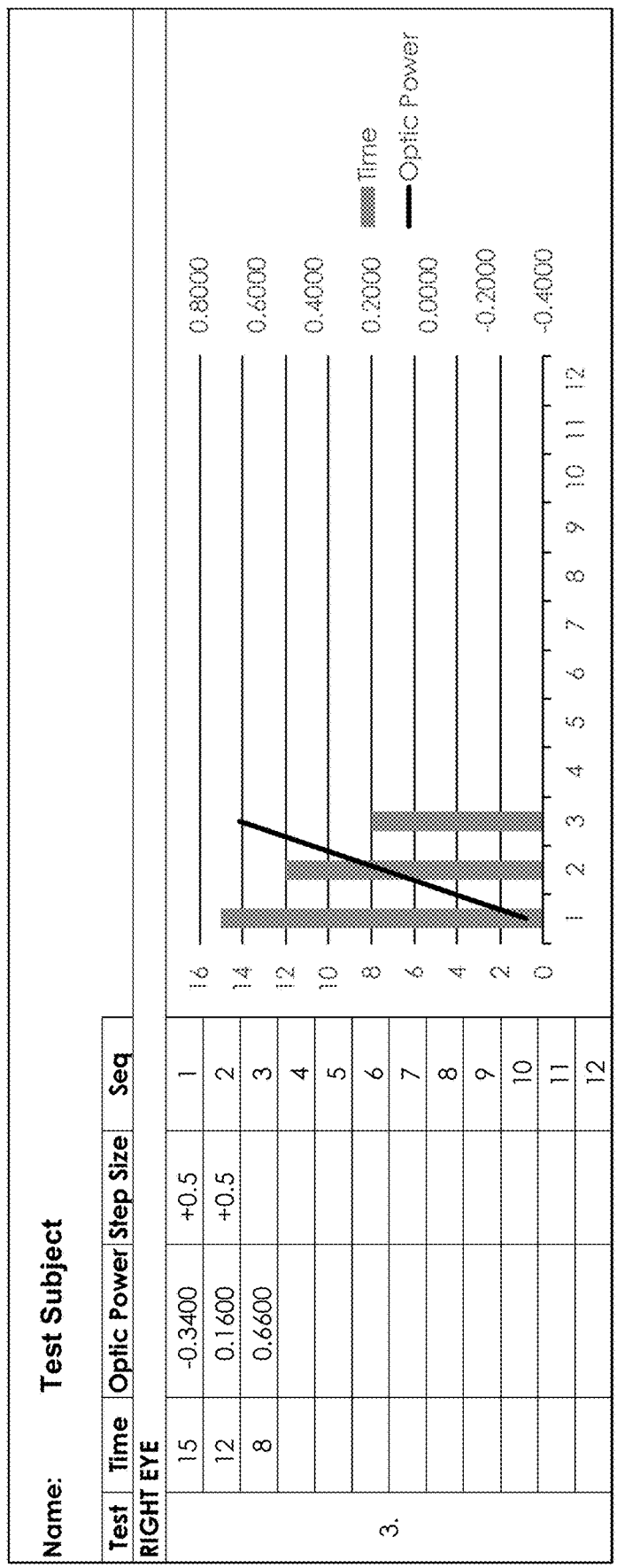
FIG. 1C illustrates a concise representation of a subjective refraction eye test that includes an example of a table indicating certain numerically essential elements of a more or less typical subjective refraction test for a test subject's right eye for ascertaining astigmatism or axis angle aberrations, wherein essential elements may include optical powers of choices of optics offered to the test subject, time durations taken by the test subject for responding, and the optics communicated by the test subject as a selection in each case from among a plurality of choices, in accordance with certain embodiments.

FIGS. 1A-1C illustrate an example of a concise presentation of a refraction eye test. In FIG. 1A, a patient was undergoing an eye test, in this case attempting to cancel the refractive errors in the sphere aberrations of the right eye. In the first column of FIG. 1A, test 1 is labeled for this data group in the testing of the sphere. In the second column, the duration in units of seconds were recorded. In this example, the patient was presented with 0.93 D sphere, at first. The last column, seq. for the test sequence numbering. In sequence 1, the patient responded after a duration of 6 seconds (column2) to indicate more minus value in sphere was preferred. In the fourth column, labeled Step size, is to mark the incremental step change in the sphere value, in this case it was set at 0.5 D. In the next test sequence, 0.5 D more minus power was presented to the patient, now at 0.43 D. Patient again requested more minus sphere power. It took patient 5 seconds this time to make that call. After a 0.5 D more minus move, the optics power is at −0.07 D, etc.

One of essential elements of refraction is to guage whether the patient is giving reliable answer, or it was just a random guess. The duration or the time for the patient to make a decision is a good measure of how confident is the patient's answer. If the duration is at 6 seconds of less for the patient to decide a choice, the patient has good confidence to provide an answer. It's answer would lead to a good final end point. Conversely, it a patient is uncertain about the answer, it may take longer period of time to decide. If the duration is over 12 seconds, it is indication that the answer can only be trust with lower level of confidence.

Hence, with a glance at the bar chart in FIG. 1A, the refractionist reviewer can tell how the test went, and should the reliability of the test be in question.

FIG. 1B illustrates the part of refraction test on the optical axis. Here, 111 degrees axis was presented to the patient. The answer from patient was "perfect for me". A "0" mark in the step size column indicates that particular test was completed. The time duration was 7 seconds for the patient to decide.

Moving on to FIG. 1C. This a test on the cylinder power on the right eye of the patient. −0.34 D was presented. It took 15 seconds to decide. Patient requested more plus cylinder power. 0.25 D cylinder was provided to the patient. The cylinder setting is now at 0.16 D. The patient still requested even more plus power. The next optics presented to the patient was 0.66 D as shown in the third column of the table. The patient took 8 seconds to decide that that value is perfect for it, and the text is completed for the cylinder power.

Figure 2A:
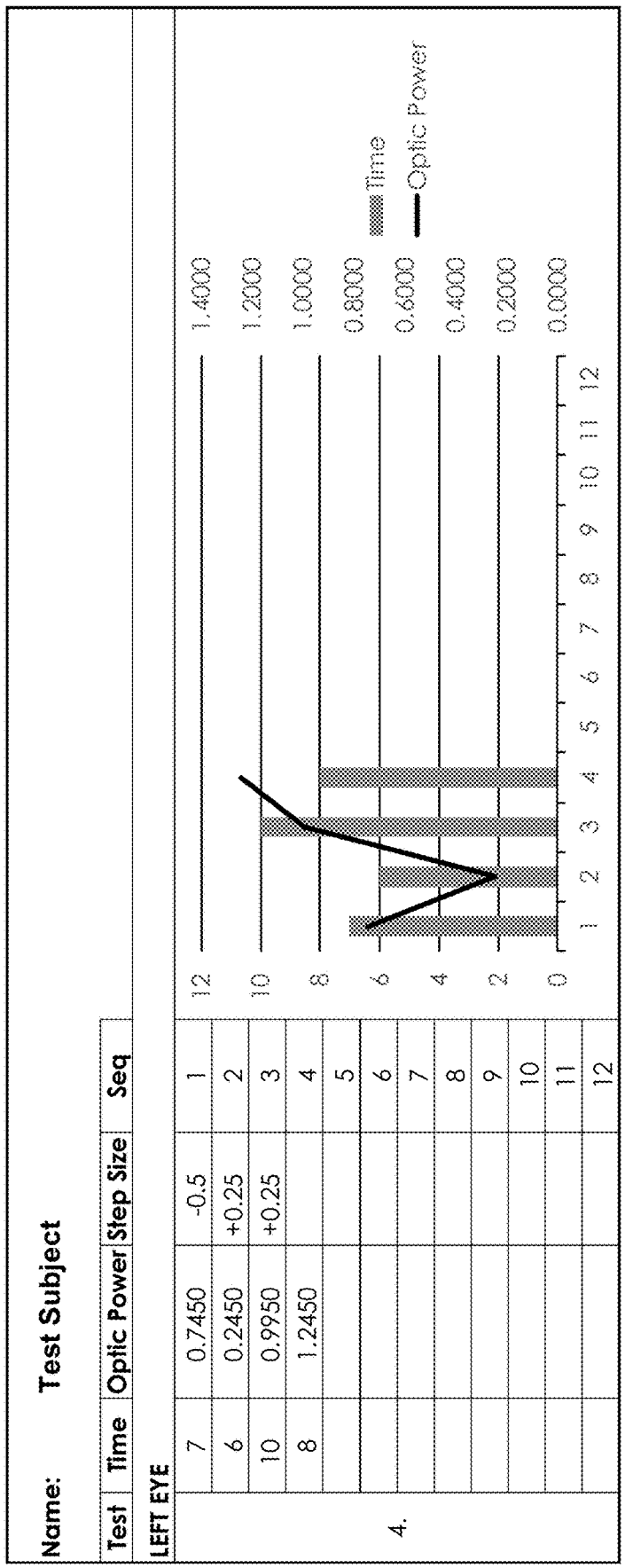
FIG. 2A includes an example of concise representation of a refraction eye test that includes a table indicating numerically essential elements of an example subjective refraction test for a test subject's right eye for ascertaining aberrations of sphere, including optical powers of choices by the test subject from among multiple optics offered to the test subject, time durations of, or intervals between, responses by the test subject, and the choices communicated by the test subject, along with a bar chart illustrating the time durations of responses of the test subject overlaying a line plot of the optical powers of the choices of optics offered to the test subject, in accordance with certain embodiments.
Figure 2B:
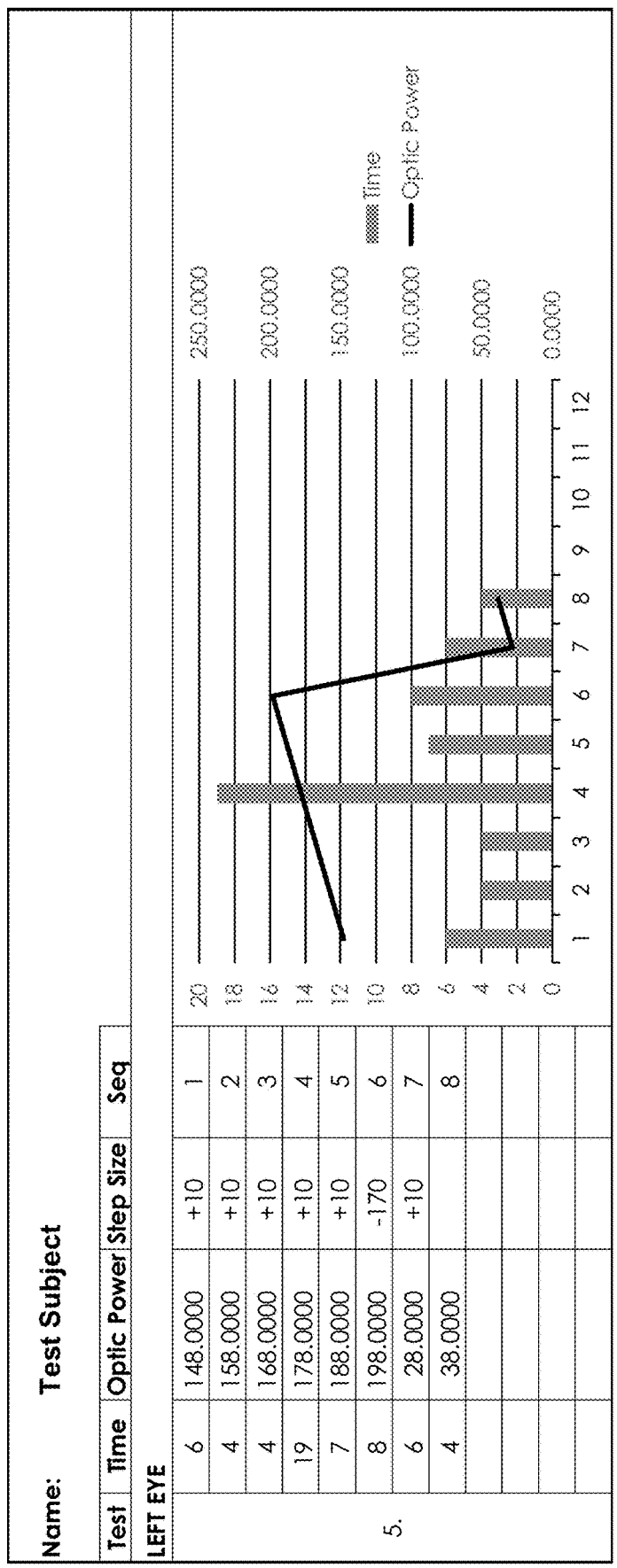
FIG. 2B includes an example of a table indicating numerically essential elements of an example subjective refraction test for a test subject's right eye for ascertaining cylinder aberrations, including optical powers of each choice of optics offered to the test subject, the time durations of each response of the test subject and the choices of optics communicated by the test subject, along with a bar chart illustrating the time durations of each response of the test subject overlaying a plot of the optical powers of the choices of optics offered to the test subject.
Figure 2C:
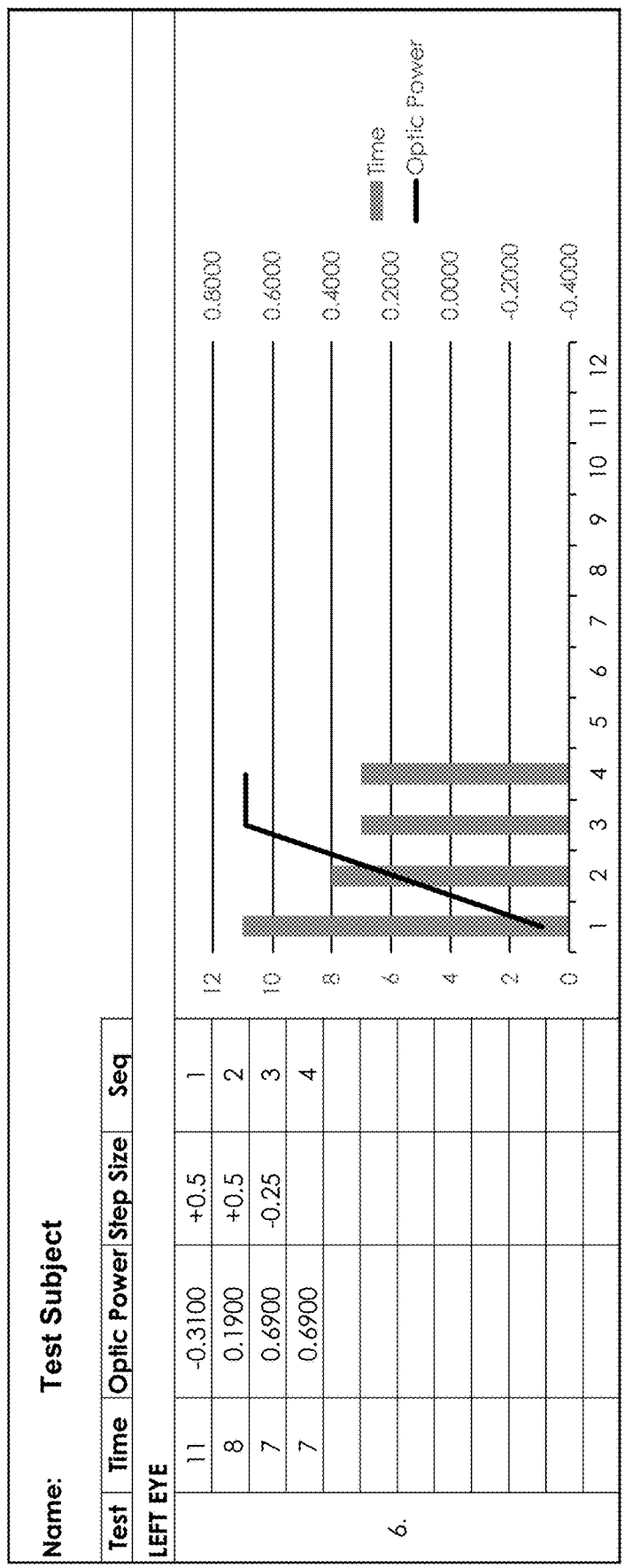
FIG. 2C includes an example of a table indicating numerically essential elements of an example subjective refraction test for a test subject's right eye for ascertaining astigmatism or axis angle aberrations, including optical powers of each choice of optics offered to the test subject, the time durations of each response of the test subject and the choices of optics communicated by the test subject, along with a bar chart illustrating the time durations of each response of the test subject overlaying a plot of the optical powers of the choices of optics offered to the test subject.

For the patient's left eye, data were illustrated in FIG. 2. FIG. 2A is to test the sphere aberrations of the patient's left eye. FIG. 2B is to test the axis angle of the astigmatism. FIG. 2C is to test the cylinder power of the patient left eye. FIGS. 2A through 2C are functionally identical to the FIGS. 1A through 1C respectively.

The representation of the eye test can be formatted in a variation of ways. In FIG. 3, the patient data are presented in a table form instead of bar charts and graphs. In the first column, the test #1 through 6 are identical in function as in FIGS. 1 and 2. Test 1 is to test the sphere aberrations of the patient's right eye, Test 2 is to test the axis, Test 3 is to test the cylinder power of the eye's aberrations. Test 4 is to test the sphere aberrations of the patient's left eye. Test 5 is to test the axis of the left eye. Test 6 is to test the cylinder power of the patient's left eye. The test sequence is in column 2. When the test changes from sphere to axis, the test sequence breaks and returns to starting from number 1. The reviewer understands that is indication of a change of test, in this case from testing sphere to testing axis. All other data point are formatted in consistency as in FIGS. 1 and 2. In the representation, one can pick out when and where in the tests that patient may experience long response time, indicating difficulties for the patient. One may use color code to highlight the cells under the time column (column 3, here) so it become obviously clear where in the entire refraction eye test. As example, one can color a time range of response time below 4 seconds in green. Color code the cells between >4 to 7 seconds in yellow. Over 7 seconds to 11 seconds in orange, and over 12 seconds in red. Such color representation tells the reviewer in one glance how confident is the patient in answering the choices in the eye test. Lots of green and yellow cells are good tests. Red and orange cells indicate patient confusion. The reliability of the test may be called to question.

In FIG. 4, another example of a refraction eye test from another patient. All columns and data formats follow those in FIG. 3.

Figure 8:
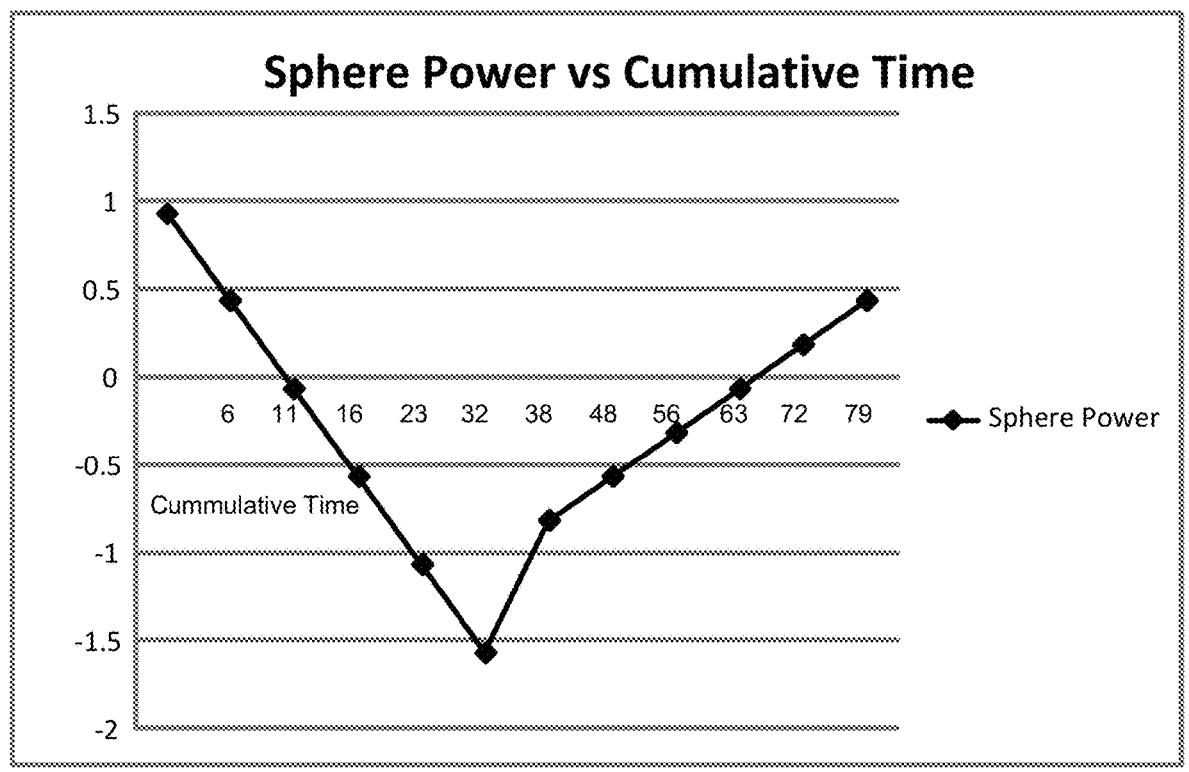
FIG. 8 includes another example of a plot using the date in Test 1 of the right eye, that show the sphere power versus the cumulative time of the test in accordance with certain embodiments.

In FIG. 8, a plot of the optics power versus the time at a certain test sequence. In this plot, the time at a sequence number is the cumulative time, not the duration time for answering one presentation of choices. In this example, data points of Test 1 in FIG. 1A is plotted. In this representation one can see the entire test 1 of FIG. 1A, starting from the first presentation of 0.93 D in sphere, in sequence 1, to 0.43 D in sequence 2, etc., to the last data point of 0.43 D in sequence 12. One can see the length of the lines joining each of the test sequence, representing the time duration specific to that test sequence. Furthermore, the overall time from sequence 1 to the last one sequence 12, took over 80 seconds. However, a reviewer who is used to looking at such plots will grash the whole sphere refraction of Test 1 in a couple of seconds by looking at the plot. Therefore, the reviewer has the benefits of "seeing" the entire test 1 in 1/40 of the total time, as if the reviewer was at the side of the patient during the test.

Returning to the example of FIGS. 1A-2C, 3 and 4, FIG. 1A includes an example of a table indicating numerically essential elements of an example subjective refraction eye test for ascertaining aberrations of sphere for a right eye of a test subject. The essential elements indicated numerically on the left hand side in FIG. 1A as a table that includes columns including information regarding essential elements of the subjective refraction eye test.

In the left-most column, an indication of a test number for a test subject are provided in the six (6) drawings FIGS. 1A, 1B, 1C, 2A,2B and-2C, or FIGS. 1A-2C, which are sequentially tests 1 thru 6 for this particular test subject. The next column to the right includes time durations taken by the test subject for communicating responses, or time intervals between responses, or alternatively, changes in time intervals between responses by the test subject before new optics are offered to the test subject based typically on the most recent previous response or the most recent 2, 3 or 4 previous responses.

The time duration taken by the test subject to communicate a response or the change of time duration or rate of change may each suggest, more or less to a refraction expert, that the test subject has indicated larger or smaller noticeable distinctions in viewing quality between sets of optics, and may suggest a proximity to optimum, and/or a direction of optimum toward which to adjust optical power and offer a new optic at the adjusted optical power, among other indications or suggestions that a trained refraction expert, such as an ophthalmologist, optometrist, optician, or geometric linear or nonlinear optics scientist, engineer or trained technician.

Each distinct optic is presented to the test subject for comparison with one or more current or previously sampled optics. The choices indicated by the test subject among the optics and patterns of choices may suggest diagnostic or prognostic techniques or analysis or next steps to a refraction expert or to a technician assisting in the test subject's performance of a subjective refraction eye test, or to the test subject herself or himself who may be using a partially or completely automated refraction instrument to generate results presentable in a concise representation on a mobile phone, tablet, reader, laptop or desktop computer or display or other graphic rendering device.

The optical power of the optics chosen by the test subject each step of the way toward an optimum optical prescription are indicated in the $3^{rd}$ column from the left in FIG. 1A. The step sizes are provided in the next column to the right in FIG. 1A. Step sizes are increments or changes in optical power between successively sampled optics. Larger step sizes are typically used at first until a certain proximity to optimum is suggested to the refraction expert or technician or to an automated-test subject following programmed instructions or systematic guidance tools or process facilitation algorithms with voice or keypad or trackball, or joystick, or mouse, or gesture recognition device proximately or remotely operated or guided by the test subject, technician or refraction expert or completely self-contained as an automatic system trained with the latest AI technology or other learning algorithms or feedback mechanism or sign-on profile driven systems that store past tests, past and/or current prescriptions and other ophthalmic information for the test subject who is recognized by the system from any of several possibly greatly spaced apart terminals, kiosks or mobile personal digital devices running appropriate application programs. Whereupon the closer the human expert senses or the automatic system calculates that a subjective refraction eye test is to the optimum corrective optic for the test subject, the smaller the step sizes will become and the greater the likelihood of incrementing back toward an optical power previously tested only this time adjusting the optical power in smaller increments until an optimum setting is determined to have been found for a particular optical aberrational parameter has been found, such as sphere (FIGS. 1A and 2A), cylinder (FIGS. 1B and 2B), or astigmatism power or axis angle (FIGS. 1C and 2C), or until a combination of such aberrational parameters has been found such as in the eye test concisely represented numerically at FIG. 3 or FIG. 4 which are example tables including sphere, cylinder and astigmatism test data together in combination tables.

FIG. 1A also includes a bar chart illustrating time durations taken by a test subject for communicating responses, or time intervals between responses that indicate or suggest a choice among multiple optics offered to the test subject. The bar chart of FIG. 1A utilizes the left vertical axis which is adjusted to include each of the 12 data points from lowest to highest appearing in the "time" column of the table $2^{nd}$ from the left most column in FIG. 1A for the response time parameter. The line plot of FIG. 1A utilizes the right vertical axis, which is adjusted to include each of the 12 data points from lowest to highest appearing in the optical power column which is 3rd from the left most column in FIG. 1A. Both the bar chart and line plot in FIG. 1A utilize the bottom horizontal axis to evenly space the twelve steps in the subjective refraction eye test illustrated in the concise representation at FIG. 1A of a test for spherical aberrational error that can be corrected by compensating for the sphere error, if any, of the right eye of this test subject using corrective contacts, glasses or an intraocular lens or using corrective laser surgery or another more or less invasive or noninvasive surgical technique based on an accurate determination of a sphere aberrational error for the test subject.

The bar chart presented in FIG. 1A is shown overlaying the plot of optical powers of selected optics indicated by the test subject during the subjective refraction eye test. The optical power starts high as the line plot shows and is reduced to a minimum at the sixth sphere adjustment step and is increased back up nearly to the starting high value at the end but at a somewhat slower rate of increase for the last half of the data points acquired and plotted in FIG. 1A compared with the rate of decrease for the first half of the data points acquired and plotted in FIG. 1A. The bar chart appears to trend from shorter response times at steps 1, 2, 3 when the optical power is highest within the data points used to illustrate this technique, to the longest response times at steps 4, 5, 6, 7, 8, and 9 plotted in the bar chart from the table of FIG. 1A, when the optical power is lowest, and back to shorter response times at higher optical powers at the end of the subjective refraction sphere aberrational error eye test at steps 10, 11, 12. The linear decrease and then substantially linear increase in optical power shown in the line plot corresponds to an oppositely trending linear increase in response time for steps 1-6 and then a similar linear response time decrease from steps 7-12.

FIG. 1B includes an example of a table indicating numerically essential elements of an example subjective refraction test for ascertaining cylinder aberrations for a right eye of a test subject. The essential elements indicated numerically in FIG. 1B include optical powers of choices by the test subject among multiple optics offered to the test subject, time durations taken by the test subject for communicating responses or time intervals between responses, and the choices indicated by the test subject in each case over a distinct option. FIG. 1B also includes a bar chart illustrating time durations taken by the test subject for communicating responses or time intervals between responses. The bar chart is presented in FIG. 1B overlaying a plot of optical powers of optics selected by the test subject from among multiple optics offered to the test subject.

FIG. 1C includes an example of a table indicating numerically essential elements of an example subjective refraction test for a test subject's right eye for ascertaining astigmatism or axis angle aberrations, including optical powers of each choice of optics offered to the test subject, time durations taken by the test subject for responding, and the optics communicated by the test subject as a selection in each case from among a plurality of choices. FIG. 1C also includes a bar chart illustrating time durations, or time intervals between responses, indicated by the test subject showing a linearly decreasing response time trend. The bar chart is shown overlaying a line plot of optical powers for the choices of corrective optics offered to the test subject during the subjective refractive eye test in the example of FIG. 1C illustrating that there is a tendency of the response times to decrease linearly with linearly increasing corrective optical astigmatism power.

FIGS. 2A-2C correspond to test for sphere, cylinder and astigmatism, respectively, for the left eye of the test subject whose right eye was tested producing the FIGS. 1A-1C described above. In FIG. 2A, increasing sphere correctional optical power appears to be associated with decreasing response times for test subjects. The cylinder test for the left eye of the test subject appears to show a linearly proportionate trend between decreasing from step 1 to step 2 the response time of the test subject or increasing from step 2 to step 3 the response time of the test subject, and decreasing from step 1 to step 2 the optical power or increasing from step 2 to step 3 the optical power. These trends suggest a certain significant, reliable corrective prescription to a refraction expert who only needs to study the data in the concise representation, assuming the data has been properly acquired, to formulate and communicate a diagnosis and/or prognosis for this test subject's left eye cylinder errors. FIG. 2C appears to indicate proportional increases in response times with increases in optical power, and decreases in response times with decreases in optical power for the left eye astigmatism of the test subject.

FIG. 2A includes an example of a table indicating numerically essential elements of an example subjective refraction test for a test subject's right eye for ascertaining aberrations of sphere, including optical powers of choices by the test subject from among multiple optics offered to the test subject, time durations of, or intervals between, responses by the test subject, and the choices communicated by the test subject. FIG. 2A also includes a bar chart illustrating the time durations of each response of the test subject overlaying a plot of the optical powers of the choices of optics offered to the test subject.

FIG. 2B includes an example of a table indicating numerically essential elements of an example subjective refraction test for a test subject's right eye for ascertaining cylinder aberrations, including optical powers of each choice of optics offered to the test subject, the time durations of each response of the test subject and the choices of optics communicated by the test subject. FIG. 2B also includes a bar chart illustrating the time durations of each response of the test subject overlaying a plot of the optical powers of the choices of optics offered to the test subject.

FIG. 2C includes an example of a table indicating numerically essential elements of an example subjective refraction test for a test subject's right eye for ascertaining astigmatism or axis angle aberrations, including optical powers of each choice of optics offered to the test subject, the time durations of each response of the test subject and the choices of optics communicated by the test subject. FIG. 2C also includes a bar chart illustrating the time durations of each response of the test subject overlaying a plot of the optical powers of the choices of optics offered to the test subject.

FIG. 3 includes an example of a table indicating numerically essential elements of another example subjective refraction eye test for ascertaining sphere, cylinder and astigmatism or axis angle aberrations for right and left eyes of a test subject. The table of FIG. 3 lists optical powers of choices among pluralities of optics offered to the test subject, the time durations taken by the test subject for communicating responses or time intervals between responses, and choices of optics indicated by the test subject over distinct options. The column of choices made by the test subject includes nullities which are indications that neither the higher nor lower power optics offered are as good as the present optic, which suggests reducing the increment of change in optical power and presenting new higher and lower power optics less spaced apart in optical power than the previous ones and still centered at the current optical power, whereas positive or negative unities suggest increasing or decreasing the optical power from which to present new optics options of respectively still higher or still lower optical power at large increments until the appropriate optical power is near enough to reduce the increments and even present both higher and lower optical power options around a potential optimal center value. Many examples beyond these are possible depending on the experience and preferences of those involved in setting up the subjective refraction eye test guidelines, those performing the test or assisting a test subject to substantially perform the test without assistance, and/or those refraction experts, which may include physicians, optometrists, and/or highly skilled, moderately skilled, or modestly skilled technicians, who will be called upon to review results and provide a diagnostic or prognostic analysis, protocol or prescription.

FIG. 4 includes an example of a table indicating numerically essential elements of another example subjective refraction test for a test subject's right and left eyes for ascertaining sphere, cylinder and astigmatism or axis angle aberrations. The table of FIG. 4 lists optical powers of choices selected among, for each choice, a plurality of optics offered to the test subject, time durations taken by the test subject for communicating responses or time intervals between responses, while alternatively total elapsed time from a common starting time may be displayed or presented, or transmitted or stored, in a table that may be similar to, but in this way distinct from, the example table illustrated at FIG. 4.

The table of FIG. 4 also includes a column including only nullities along with a few positive and negative unities. The null entries may represent an indication by the test subject of no preference or alternatively favoring the status quo, while an indication of positive unity suggests a next optic with increased optical power and an indication of negative unity suggests a next optic of lower optical power, or alternatively, positive unity may suggest continuing to change optical power in a same direction, while negative unity may suggest reversing a direction of change of optical power back towards a previous optic that is now favorably indicated over a current choice, while another option may permit positive and negative dualities and/or their multiplicative inverses, i.e., plus half and minus half as indications by the test subject to adjust optical power more or less drastically than the last change of optical power.

Figure 5:
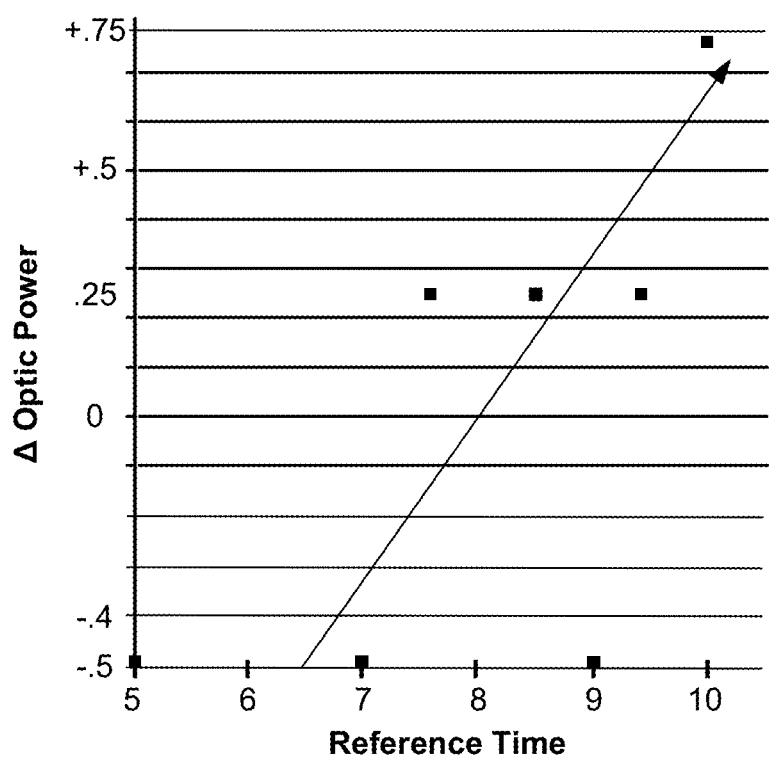
FIG. 5 includes an example of a stand-alone concise representation or one component of a multi-component concise representation of a subjective refraction eye test including a plot of changes in optical power versus response times for a portion of an example subjective refraction test in accordance with certain embodiments, with the trend appearing to be linear and with positive slope.

FIG. 5 includes a plot of changes in optical power versus response times for a portion of an example subjective refraction test in accordance with certain embodiments. The trend appears to be linear and with positive slope.

Figure 6:
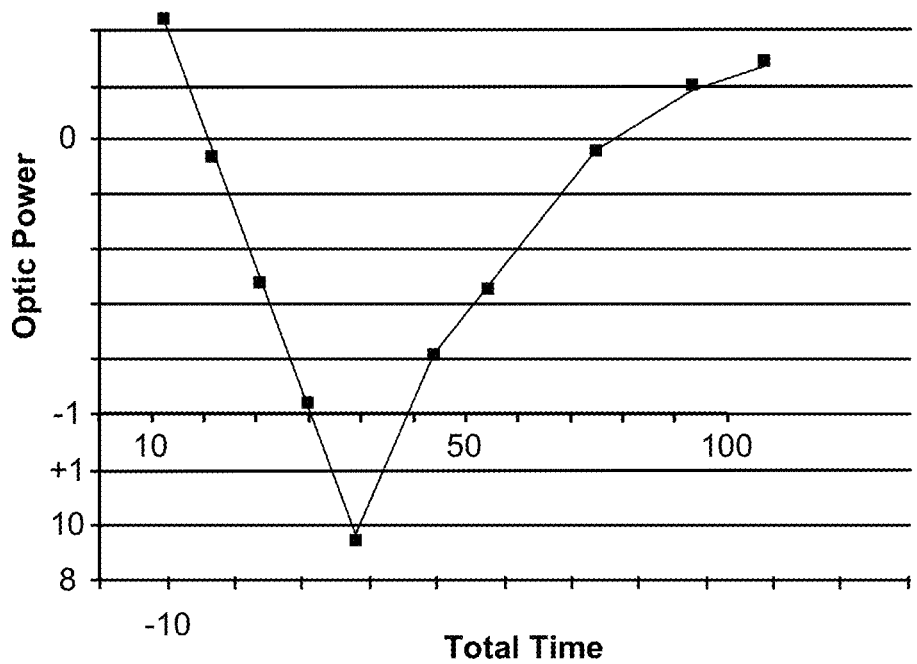
FIG. 6 includes an example of another stand-alone concise representation or one component of a multiple component concise representation that includes a plot of optical power versus total response time for a portion of an example subjective refraction test in accordance with certain embodiments.

FIG. 6 includes a plot of optical power versus total response time for a portion of an example subjective refraction test in accordance with certain embodiments. The trend appears to be "V" shaped, including linearly decreasing optic power with total time for the first 35 seconds of the subjective refraction eye test illustrated in FIGS. 4 and 6, and then a linear increasing to logarithmic or reverse parabolic trend with positive slope is shown in FIG. 6 after 35 seconds out to 100 seconds or so.

Figure 7:
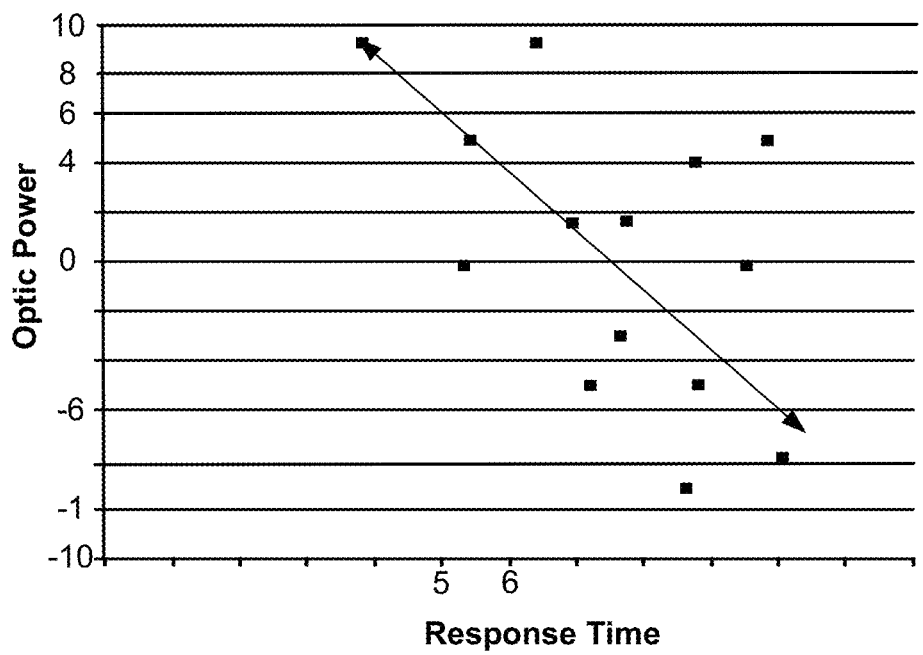
FIG. 7 includes another example of a stand-alone concise representation or a component of a multiple component concise representation that includes a plot of optical power versus response time for a portion of an example subjective refraction test in accordance with certain embodiments.

FIG. 7 includes a plot of optical power versus response time for a portion of an example subjective refraction test in accordance with certain embodiments. A trend is shown whereby the optic power appears to decrease linearly with increasing response time, similar to the trend shown in FIGS. 1A and 1C and described in some detail above.

FIG. 8 includes a plot using the date in Test 1 of the right eye, that show the sphere power versus the cumulative time of the test. The Horizonal axis is for Cumulative Time. Vertical axis is Sphere Power.

While an exemplary drawing and specific embodiments of the present invention have been described and illustrated, it is to be understood that that the scope of the present invention is not to be limited to the particular embodiments discussed. Thus, the embodiments shall be regarded as illustrative rather than restrictive, and it should be understood that variations may be made in those embodiments by workers skilled in the arts without departing from the scope of the present invention, as set forth in the claims below and structural and functional equivalents thereof.

In addition, in methods that may be performed according to preferred embodiments herein and that may have been described above, the operations have been described in selected typographical sequences. However, the sequences have been selected and so ordered for typographical convenience and are not intended to imply any particular order for performing the operations, unless expressly set forth or understood by those skilled in the art being necessary.

I claim:

1. A method of preparing a representation of a subjective refraction eye test for review by an optometrist or physician that includes an evaluation of reliability of patient responses, comprising:
   (a) capturing elements of a subjective refraction eye test, including:
      (i) choices of optical lenses offered to the patient;
      (ii) responses of the patient to the choices of optical lenses presented to said patient; and
      (iii) indications of degrees of reliability of one or more of said responses of the patient to the choices of optical lenses presented to the patient;
   (b) generating a representation of said subjective refraction test including a presentation that illustrates said elements, and
   (c) wherein said presentation comprises one or more charts, plots, or graphs, or combinations thereof, that each illustrate one or more of said elements at least including a chart, plot or graph, or combinations thereof, that illustrates optical powers of said choices of optical lenses offered to the patient and said responses of the patient along with one or more of said indications of degrees of reliability, ascertained from said one or more of said responses of the patient to the choices of optical lenses presented to the patient in the subjective refraction test,
   wherein said indications of degrees of reliability of said responses of said patient comprise time durations of said responses of the patient to the choices of optical lenses presented to the patient in the subjective refraction test.

2. The method of claim 1, wherein said presentation comprises one or more charts, plots or graphs, or combinations thereof, that illustrates said time durations of said responses of the patient.

3. The method of claim 2, wherein said time durations are categorized into time duration ranges, and categories of said time duration ranges include (i) 4seconds or less, (ii) more than 4 seconds to 7 seconds, (iii) more than 7 seconds to 11 seconds, and (iv) over 11 seconds.

4. The method of claim 2, wherein categories of time duration ranges are color-coded within said presentation.

5. The method of claim 1, wherein said presentation further comprises a bar chart illustrating said time durations of said responses of the patient.

6. The method of claim 5, wherein said presentation further comprises a plot of optical powers selected by the patient overlaying said bar chart.

7. The method of claim 1, wherein said presentation comprises data points of optical powers selected by the patient that are spaced along a time axis in accordance with said time durations of said responses of the patient.

8. A method of preparing a representation of a subjective refraction eye test for review by an optometrist or physician that includes an evaluation of reliability of patient responses, comprising:
   (a) capturing elements of a subjective refraction eye test, including:
      (i) choices of optical lenses offered to the patient;
      (ii) responses of the patient to the choices of optical lenses presented to said patient; and
      (iii) indications of degrees of reliability of one or more of said responses of the patient to the choices of optical lenses presented to the patient;
   (b) generating a representation of said subjective refraction test including a presentation that illustrates said elements, and
   (c) wherein said presentation comprises one or more charts, plots, or graphs, or combinations thereof, that each illustrate one or more of said elements at least including a chart, plot or graph, or combinations thereof, that illustrates optical powers of said choices of optical lenses offered to the patient and said responses of the patient along with one or more of said indications of degrees of reliability, ascertained from said one or more of said responses of the patient to the choices of optical lenses presented to the patient in the subjective refraction test,
   wherein the method comprises color coding said degrees of reliability of said responses of the patient, such as to indicate either, that the subjective refraction test is a good test or that a reliability of the subjective refraction test is called into question.

9. The method of claim 8, wherein said presentation further comprises one or more tables indicating numerically one or more of said elements at least including a table indicating numerically optical powers of said choices of optical lenses offered to said patient and responses of the patient.

10. The method of claim 8, wherein said presentation further comprises one or more charts, plots or graphs, or combinations thereof, identified as being for the left eye or right eye, or both, of the patient.

11. The method of claim 8, wherein said elements further comprise step sizes of changes in optical power between successive choices of optical lenses offered to the patient.

12. A method of preparing a representation of a subjective refraction eye test for review by an optometrist or physician, comprising:
 (a) capturing elements of a subjective refraction eye test, including:
  (i) choices of optical lenses offered to the patient; and
  (ii) responses of the patient;
 (b) generating a representation of said test including a presentation that illustrates said elements,
 (c) wherein said presentation comprises one or more charts, plots, or graphs, or combinations thereof, that each illustrate one or more of said elements at least including a chart, plot or graph, or combinations thereof, that illustrates optical powers of said choices of optical lenses offered to the patient and said responses of the patient,
wherein said presentation comprises a continuous audio recording or assembly of audio clips of patient responses to said choices of optical lenses and a graphical presentation illustrating said choices of optical lenses or said patient response times or both.

13. A method of preparing a representation of a subjective refraction eye test for review by an optometrist or physician, comprising:
 (a) capturing elements of a subjective refraction eye test, including:
  (i) choices of optical lenses offered to the patient; and
  (ii) responses of the patient;
 (b) generating a representation of said test including a presentation that illustrates said elements,
 (c) wherein said presentation comprises one or more charts, plots, or graphs, or combinations thereof, that each illustrate one or more of said elements at least including a chart, plot or graph, or combinations thereof, that illustrates optical powers of said choices of optical lenses offered to the patient and said responses of the patient,
wherein said presentation comprises a continuous video recording or assembly of video clips or a slide show of still images showing patient responses to said choices of optical lenses and a graphical presentation illustrating said choices of optical lenses or said patient response times or both.

14. A representation of a subjective refraction eye test for communicating to an optometrist or physician for review that includes an evaluation of reliability of patient responses, comprising:
 (a) a presentation that illustrates elements of the test, the elements including:
  (i) choices of optical lenses offered to the patient;
  (ii) responses of the patient to the choices of optical lenses presented to said patient; and
  (iii) indications of degrees of reliability of one or more of said responses of the patient to the choices of optical lenses presented to the patient;
 (b) wherein said presentation comprises one or more charts, plots, or graphs, or combinations thereof, that illustrate said elements at least including a chart, plot or graph, or combinations thereof, that illustrates optical powers of said choices of optical lenses offered to the patient and said responses of the patient along with one or more of said indications of degrees of reliability, ascertained from one or more of said responses of the patient to the choices of optical lenses presented to the patient in the subjective refraction test,
wherein said presentation comprises a bar chart illustrating said indications of degrees of reliability of said responses of the patient overlaying a plot of optical powers selected by the patient.

15. The representation of claim 14, wherein the elements of said test further include time durations of some or all of the responses of the patient when said patient is presented with choices of optical lenses.

16. A processor-based device, comprising:
 (a) a processor;
 (b) one or more non-transitory processor-readable digital storage devices having code embedded therein for programming said processor to perform a method of preparing a digital representation of a subjective refraction eye test for review by an optometrist or physician according to claim 14; and
 (c) electronics configured for one or more of transmitting, displaying, storing, translating or editing said representation of said subjective refraction eye test for said review by said optometrist or physician.

17. A representation of a subjective refraction eye test for communicating to an optometrist or physician for review that includes an evaluation of reliability of patient responses, comprising:
 (a) a presentation that illustrates elements of the test, the elements including:
  (i) choices of optical lenses offered to the patient;
  (ii) responses of the patient to the choices of optical lenses presented to said patient; and
  (iii) indications of degrees of reliability of one or more of said responses of the patient to the choices of optical lenses presented to the patient;
 (b) wherein said presentation comprises one or more charts, plots, or graphs, or combinations thereof, that illustrate said elements at least including a chart, plot or graph, or combinations thereof, that illustrates optical powers of said choices of optical lenses offered to the patient and said responses of the patient along with one or more of said indications of degrees of reliability, ascertained from one or more of said responses of the patient to the choices of optical lenses presented to the patient in the subjective refraction test,
wherein said indications of degrees of reliability of said responses of said patient comprise time durations of said responses of the patient to the choices of optical lenses presented to the patient in the subjective refraction test.

18. The representation of claim 17, wherein said time durations of said responses of the patient are categorized within time duration ranges which include (i) 4 seconds or less, (ii) more than 4 seconds to 7 seconds, (iii) more than 7 seconds to 11 seconds, and (iv) over 11 seconds.

19. The representation of claim 17, wherein categories of time duration ranges of said responses of the patient are color-coded.

20. A representation of a subjective refraction eye test for communicating to an optometrist or physician for review that includes an evaluation of reliability of patient responses, comprising:

(a) a presentation that illustrates elements of the test, the elements including:
(i) choices of optical lenses offered to the patient;
(ii) responses of the patient to the choices of optical lenses presented to said patient; and
(iii) indications of degrees of reliability of one or more of said responses of the patient to the choices of optical lenses presented to the patient;
(b) wherein said presentation comprises one or more charts, plots, or graphs, or combinations thereof, that illustrate said elements at least including a chart, plot or graph, or combinations thereof, that illustrates optical powers of said choices of optical lenses offered to the patient and said responses of the patient along with one or more of said indications of degrees of reliability, ascertained from one or more of said responses of the patient to the choices of optical lenses presented to the patient in the subjective refraction test,
wherein said indications of degrees of reliability of said responses of the patient are categorized within time duration ranges which are color coded.

21. A representation of a subjective refraction eye test for communicating to an optometrist or physician for review that includes an evaluation of reliability of patient responses, comprising:
(a) a presentation that illustrates elements of the test, the elements including:
(i) choices of optical lenses offered to the patient;
(ii) responses of the patient to the choices of optical lenses presented to said patient; and
(iii) indications of degrees of reliability of one or more of said responses of the patient to the choices of optical lenses presented to the patient;
(b) wherein said presentation comprises one or more charts, plots, or graphs, or combinations thereof, that illustrate said elements at least including a chart, plot or graph, or combinations thereof, that illustrates optical powers of said choices of optical lenses offered to the patient and said responses of the patient along with one or more of said indications of degrees of reliability, ascertained from one or more of said responses of the patient to the choices of optical lenses presented to the patient in the subjective refraction test,
wherein evaluation of degrees of reliability of said responses of the patient are color coded, such as to indicate either that the subjective refraction test is a good test or that a reliability of the subjective refraction test is called into question.

22. The representation of claim 21, wherein the elements of said test further include time durations of some or all of the responses of the patient when said patient is presented with choices of optical lenses.

23. The representation of claim 21, wherein said indications of degrees of reliability of said responses of said patient comprise time durations of said responses of the patient to the choices of optical lenses presented to the patient in the subjective refraction test.

24. The representation of claim 21, wherein said time durations of said responses of the patient are categorized within time duration ranges which include (i) 4 seconds or less, (ii) more than 4 seconds to 7 seconds, (iii) more than 7 seconds to 11 seconds, and (iv) over 11seconds.

25. The representation of claim 21, wherein categories of time duration ranges of said responses of the patient are color-coded.

26. The representation of claim 21, wherein said indications of degrees of reliability of said responses of the patient are categorized within time duration ranges which are color coded.

* * * * *